| United States Patent [19] | [11] Patent Number: 4,719,111 |
| Wilson | [45] Date of Patent: Jan. 12, 1988 |

[54] NOVEL COMPOSITION FOR TREATMENT OF DECUBITUS ULCERS

[76] Inventor: Lynn M. Wilson, 3731 Nelson Ave., Blasdell, N.Y. 14219

[21] Appl. No.: 744,619

[22] Filed: Jun. 14, 1985

[51] Int. Cl.$^4$ .................. A61K 35/78; A61K 31/685
[52] U.S. Cl. .................................. 424/195.1; 514/78; 514/925; 514/969
[58] Field of Search .............. 424/195.1; 514/78, 925, 514/969

[56] References Cited
PUBLICATIONS

Chem. Abst., 101:169304s, 1984.

*Primary Examiner*—J. R. Brown
*Assistant Examiner*—John W. Rollins, Jr.
*Attorney, Agent, or Firm*—James J. Ralabate

[57] ABSTRACT

A composition for treatment of decubitus ulcers comprising an admixture of from about 10 to about 50 parts lecithin, from about 10 to about 50 parts goldenseal root or rhizome, and from about 10 to about 50 parts myrrh gum.

10 Claims, No Drawings

NOVEL COMPOSITION FOR TREATMENT OF DECUBITUS ULCERS

This invention relates to a novel composition and, more specifically, to a formulation useful in the treatment of skin ulcers including decubitus ulcers or bed sores.

BACKGROUND OF THE INVENTION

In nursing homes, hospitals or in private homes where invalid patients with certain diseases and afflictions are bedridden, a problem arises from bed sores which these patients develop. These bed sores or decubitus ulcers usually result from a loss of blood circulation caused by pressure on the skin, particularly pressure over a bony protuberance. The pressure on areas of support exceeds the mean capillary blood pressure and these areas are vulnerable to the decubitus ulcers. Other factors which can contribute to decubitus ulcers are lack of proper ventilation, moisture and diet. Additionally, the problem of bed wetting and the accumulation of urine in the bed contribute to the bed sores of the patient since the moisture remains in the area of the patient's body. There have been attempts to remedy these conditions and prevent the decubitus ulcers, but some of these have been relatively commercially unsuccessful. Some have involved merely the passing of air through the bed mattress which air is then allowed to pass upwardly around the patient's body. Other devices have had pulsatingly inflatable air mattresses which again merely allow the air to be circulated upwardly around the body of the patient. Some of the more acceptable devices useful in the treatment of bed sores are the Clinitron Therapy method provided by Support Systems International, Inc. of Charleston, South Carolina, and dental irrigating devices described in an article on pages 303–305 of the September/October 1984 Vol. 33, No. 5 issue of *Nursing Research*. Other devices to treat decubitus ulcers include whirlpools, air mattresses, heel and elbow sheepskin protectors, heat lamps, foot boards, and draw sheets. While some of these units have desirable characteristics, they also possess serious drawbacks. Some of the disadvantages of these devices are as follows: Whirlpools can lead to possible infection or reinfection unless a completely sterile environment is maintained. Air mattresses have caused pressure points in obese patients, heel and elbow protectors reduce friction but are found to be not as well padded in the areas needed most, and also may retain moisture, therefore promoting maceration. The Clinitron Flotation System is an excellent preventative measure, but is so expensive that most facilities only have one unit, or none at all, and is not practical since it cannot be moved up and down. Overhead trapeze bars can only be used by responsive patients. Heatlamps can cause severe burns if not watched intensely, and need to be used every eight hours.

Some supportive measures used to prevent decubiti are: occupational therapy, physical therapy, nutritional therapy, and tissue assessment on admission. Some physical measures used to prevent these pressure sores are as follows: a repositioning schedule every two hours, checking bony prominences for breakdown daily, keeping skin dry and clean, ambulating patient as much as possible, forcing fluids, and using cornstarch to prevent friction.

Decubitus ulcers are staged according to severity:

Stage I—Skin pink-mottled, the epidermis is damaged.
Stage II—Skin is cracked, blistered and broken, the epidermis is destroyed.
Stage III—Skin is broken with some tissue involvement. The sub-cutaneous skin is destroyed and there are decaying cells.
Stage IV—Extensive penetration to muscle and bone, presence of necrotic tissue, and profuse drainage. Structures are decayed. By stage III or IV, debridement is usually necessary.

Discussions of decubitus ulcers and their treatment can be found in the following journal articles:

1. Mikulic, M. A. Treatment of pressure ulcers. *Am. J. Nurs.* 80:1125–28, June, 1980.
2. Love-Mignogna, S., and Wind, S. Decubitus ulcers and the Karaya treatment program. *ONAJ.* 5:17–18, Sept. 1978.
3. Berecek, K. H. Treatment of decubitus ulcers. *Nurs. Clin. North Am.* 10:171–210, March 1975.
4. Rhodes, B., and others. The treatment of pressure sores in geriatic patients: a trial of sterculia powder. *Nurs. Times* 75:365–368, Mar. 1, 1979.
5. Kavchak-Keyes, M. A. Treating decubitus ulcers using four proven steps. *Nurs. 77* 77:44–45, Oct. 1977.
6. Lee, B. Y., and others. Topical application of providone-iodine in the management of decubitus and stasis ulcers. *J. Am. Geriatr. Soc.* 27:307:306, July 1979.
7. Hyland, D. B., and Kirkland, V. J. Infrared therapy for skin ulcers. *Am. J. Nurs.* 80:1800–1817, October 1980.
8. Connel, J. F., and Rousselot, J. M. Povidineiodine extensive surgical evaluation of a new antiseptic agent. *Am. J. Surg.* 108:849–855, December 1964.
9. Morely, M. 16 steps to better decubitus ulcer care. *Can. Nurse* 77:29–33, July–August, 1981.

There are many different products available for the care of decubitus ulcers. Some of these are Betadine Solution Wash, Uniwash, Duoderm, Op-site, the Bard Absorption dressing, water repellent ointments, Dakins Solution as a wash, Elase, antacids, Deprisan as a medicated dressing and Domeboros Solution. Betadine solution rinses are good for their antibacterial properties, but some allergic reactions can occur to the iodine, enhancing the skin problem. Uniwash and Uniderm treatments have to be done every eight hours or more frequently. Dressings are necessary and beneficial but sometimes tear the skin further. Medicated dressings such as Silvadene have to be changed also every eight hours. Domeboros Solution is used every four hours during the day. Antacids may be beneficial for superficial ulcers, but can hold in purlent matter and debris in the deep ulcer.

Thus, decubitus ulcers, otherwise known as "bedsores", are an age old problem. Treatment is usually a uniform and standard nursing treatment in a facility, but prevention is the best cure. Although not all bedsores can be blamed on nursing care because many are not preventable, there are an estimated 3,000,000 pressure sores in the U.S.A. yearly. In 1983, an estimated $8,000,000,000.00 were spent on treating pressure sores.

Patients prone to these problems are cachetic patients (those in negative nitrogen balance), patients with congenital or acquired boney deformaties, stroke patients who are immobile, paraplegics with uncontrollable muscle spasms, any spinal cord injury patient, incontinent patients, arthritic patients, those who are confused or comatose, nutritionally deficited patients, those with edema or poor capillary refill, anyone who is on medications such as steroids, tranquilizers and analgesics, any geriatric patient, and anyone with pre-existing diseases.

These decubiti also result from friction, shearing force and pressure, which all hospital patients are exposed to while in bed. Usually, a combination of two of those forces will cause a pressure sore and it can happen in a twelve hour period. Friction can be from moving in bed, shearing can be from a position in bed, and pressure can be from gravity alone. A pressure of greater than 25 mm Hg. will occlude flow of blood to capillaries in soft tissues causing hypoxia and, if unrelieved, eventual necrosis.

Fluid filled beds alone cannot prevent pressure sores. The waterproof covering that encases the fluid in the bed does not allow moisture from the patient's skin to evaporate so mild to moderate sweating actually promotes friction when the patient moves. Preventative devices can only delay the development of pressure sores. Fluid filled beds cause hip flexion possibly leading to contractures and pooling of pelvic blood. Alternating pressure mattresses and gel flotation pads reduce pressure but not enough to maintain adequate blood flow to all capillaries.

SUMMARY OF THE INVENTION

It is therefore an object of this invention to provide a novel composition for the treatment of decubitus ulcers devoid of the above-noted disadvantages.

Another object of this invention is to provide a novel formulation useful in the treatment of decubitus ulcers that is easy to use and relatively inexpensive.

A further object of this invention is to provide a novel composition having antiseptic and recuperative properties relative to decubitus ulcers.

Another object of this invention is to provide an effective means to treat decubitus ulcers even those in patients who are relatively immobile.

Still another object of this invention is to provide a composition for the treatment of bed sores that assists in the subsequent formation of granulation tissue.

Another still further object is to provide a composition that could assist in increasing the blood circulation in patients affected with decubitus ulcers.

These and other objects of this invention are provides generally speaking, by a novel composition hereinafter referred to as a packing material. The packing material or formulation comprises from about 10-50 parts lecithin, from about 10-50 parts myrrh gum, and from about 10-50 parts golden seal. All parts and percentages in this disclosure relate to parts by weight and percentage by weight. Before the packing material is applied to a patient, it is preferable to wash the sore with a suitable washing compound.

The wash combination of ingredients must have the following properties:
germicidal
antiseptic
astringent
antibacterial
antifungal
debridement
granulation formation The packing formulation of this invention has many advantages because of its combination of ingredients and the minimal treatment that is required. Properties of the packing that are beneficial are as follows:
emulsifying
antioxidant
astringent
antiseptic
tonic
topical stimulant
anti-inflammatory
aiding nervous system integrity
reducing catarrhal conditions
increasing circulation
increasing granulation tissue of mucous membranes.

Benefits of this packing formulation as a treatment for decubitus ulcers and possible other skin ulcers is that it is an extremely fast method of promoting granulation tissue, enhancing circulation, and improving sensation in patients affected with these menaces. It is easily applied with a minimal amount of daily care and expense. These ingredients can be contained with a minimal loss of spillage, can be produced with a protection against environmental hazards, and can be free from interaction between container and product in plastic dispenser.

Recent international delegations discussing research of natural products has led to an ever-increasing interest channeled in their direction. Therapeutic care dependent upon identification of medically effective elements and development of synthetic drugs with these elements is an expanding area of medicine. Medical schools, hospitals and institutes are expanding the traditional medicine interest. The importance of a product such as this is that of speed in the growth of granulating tissue which was on the average at about 1/16 inch per day. It is an incredibly fast mode of treatment for stage II-IV ulcers. However, the packing formulation of this invention should be used only after proper removal of any necrotic tissue which is present. Proper removal of necrotic tissue should be done under the supervision of a physician and may include surgical debridement.

A preferred wash solution to be used before using the packing formulation of this invention comprises hydrogen peroxide, normal saline solution, witch hazel, and boric acid. These ingredients are described as follows:

Hydrogen peroxide, also known as hydrogen dioxide or hydropic oxide, is a colorless liquid without odor having a slightly acid taste. In the presence of oxidizable substances and firments, $H_2O_2$ (hydrogen peroxide) has the tendency to decompose into $H_2O$ and $O_2$ It also decomposes readily when heated and is soluble in $H_2O$, alcohol and ether. Dilute solutions are less stable.

Composition: Hydrogen 5.94%; Oxygen 94.06%
Actions: Molecular weight 34.02.

The germicidal actions of $H_2O_2$ is due to its strong oxidizing power. When it contacts with tissues, however, its germicidal powers are limited, owing to the fact that organic matter decomposes it. It is of value chiefly as a cleansing agent for suppurating wounds and inflamed mucous membranes. It is especially useful for this purpose because of the development of gas which tends to loosen adherent deposits. Uses are therefore as topical antiseptic, anti-infective, and a cleansing agent.

Boric acid, or otherwise known as orthoboric acid or borofax is a colorless, odorless, transparent crystal.
Composition:
Boric acid: 17.50% ph 5.1
Hydrogen: 4.88%
Oxygen: 77.62%
Molecular wt.: 61.84%
Abbreviation: $H_3BO_3$ Actions: The antibacterial, astringent, antiseptic and antifungal properties of this is beneficial for the cleansing of wounds. It is used chiefly in an aqueous solution or power for external use. Human toxicity can be caused by ingestion or absorption of this product. Boric acid is used in food products as a preservative, soaps and cosmetics.

Medical Use: Skin conditions; no interactions have been recorded with any drugs.

Normal saline solution or sodium chloride solution is an isotonic solution used in irrigations. It aids in the formation of granulation tissue, promotes healing and also has debridement properties. Normal saline 0.9% is a sterile solution distributed in liter bottles. It has 154 mg. NA and 154 mg CL per liter or fluid (sterile salt water). Example: 0.9% NaCl Irrigation, VSP. By Travenol Labs, Deerfield, Illinois 60015.

Witch hazel, or otherwise known as Hamamdis water or Hamamdis Virginiana, is from a shrub or tree that is of the hoja de Hamamelis species. It is found in the U.S.A. and Canada. The medication is made from the bark and leaves. The bark contains 6% tannin which is composed of crystalline Hamameli tannin, free gallic acid and a small quantity of amorphous phlobatannin. Merck reports the drug contains: 0.2% chloride, a saponin, and a glycoside.

Uses: The tannins are all protein precipitants with astringent, hemostatic and antiseptic properties. Witch hazel is used as a mild astringent in ointments, solutions and suppositories. Most common use is for hemorrhoids. Other indications are for anal discharge, diaper rash and itching. No interactions of significance have been reported. The only sensitivity to watch for is redness or swelling.

Each of the below listed formulations can be used to effectively treat a patient with decubitus ulcers.

I. Wash:
  35% $H_2O_2$
  35% normal saline
  15% witch hazel
  15% boric acid
Packing:
  35% lecithin
  35% goldenseal
  30% myrrh gum II. Wash:
  45% $H_2O_2$
  45% normal saline
  5% witch hazel
  5% boric acid
Packing:
  40% lecithin
  40% goldenseal
  30% myrrh gum III. Wash:
  43% $H_2O_2$
  43% normal saline
  7% witch hazel
  7% boric acid
Packing:
  35% lecithin
  35% myrrh gum
  30% goldenseal IV. Wash:
  40% $H_2O_2$
  40% normal saline
  10% witch hazel
  10% boric acid
Packing:
  $33\frac{1}{3}$%, lecithin
  $33\frac{1}{3}$% goldenseal
  $33\frac{1}{3}$% myrrh gum The ingredients of both the wash and packing formulation of this invention are easily packed and stored for use or shipment. The wash will come pre-mixed, in a sterile 250 cc–500 cc container. Also, a 30 cc sterile syringe will be included and sized so that it can fit easily into the mouth of the solution container and used for irrigation of ulcer. The packing will come in a sterile 250 cc container, and be ½ filled with the needed sterile ingredients. Along with the container will come a 50 cc syringe filled with normal saline. This syringe of saline will be used to mix with the dry ingredients and form a packing. There will also be a pair of sterile gloves included and 2–3 sterile tongue blades.

In treating a patient, the following procedure is generally used. Patient is positioned on side, or so that there is easier access to wound site. All materials are opened which are needed for procedure. With sterile technique, irrigate wound with wash solution, using irrigating syringe included. Repeat once. Keep patient properly positioned. The 50 cc syringe of normal saline is dispensed directly into the dry ingredients using enough only to make a somewhat pastelike consistency. Maintain sterile technique by mixing it with enclosed tongue blade. Save any leftover normal saline for next use. Sterile gloves are donned with proper technique and the ulcer is packed with pastelike mixture using sterile tongue blade. Any sinus areas are also packed. It is covered with a sterile gauze 4×4 dressing or 4×4 pad and left on for four days. If incontinence is a problem the 4×4 is reinforced with ABD or Telfa Dressing to prevent cross contamination of wound. Extra packing is refrigerated for next use.

After four days, the packing is removed from refrigerator and warmed to room temperature before use. If needed, some of leftover normal saline is added to give packing more moisture. (It tends to dry out in refrigerator.) Remove old packing. Irrigate ulcer with wash provided at least twice and repack wound as originally instructed. For duration of wound care, wash and pack wound three times per week.

EXAMPLES AND PREFERRED EMBODIMENT

Any suitable lecithin, 95% phosphatides, goldenseal or myrrh gum may be used in the packing formulation of this invention. Each of these ingredients are known chemicals and can be easily obtained in the market place.

"Goldenseal" or otherwise known as yellow puccoon, ground raspberry, turmeric root, hydrastis, yellowroot, orangeroot, jaundice root, Ohio curuma, yellow wort, eyebalm, eyebright, eyeroot, goldenroot, Indian dye, Indian paint and Indian turmeric is from the hydrastis family. It is a small perennial, hardy plant found in the well-drained woodlands of North America east of the Mississippi. Also, it is cultivated in the state of Washington and in Europe. It needs to lie in well fertilized soil containing abundant leaf mold and needs protection from high heat and light in the summer. Ideally, the sloping side of a woodland hill where shade is abundant and drainage is good. The dried rhizome (part just below the surface) and roots are the medicinal parts of this plant. The root stalks are harvested in the fall and the leaves and tops in late summer. Goldenseal has a slight odor and bitter taste. The roots of this plant show a suberized hypodermis, a starch containing cortex, lignified endodermis and a small central wood with 2-6 rays. The root contains at least three alkaloids, namely:

Hydrastine: $C_2N_2O_6N$
Berberine: $C_{20}H_{19}O_5N$
Canadine: $C_{20}H_2ON$

It also contains resin, albumen, starch, fats, sugar and a volatile oil.

Goldenseal is one of the best substitutes for quinine. It influences mucous membranes and tissue with which it comes in contact. Beneficial physiological effects are:
Increasing circulation
Rehabilitation of mucous membranes
Anti-inflammation
Reducing catarrhal conditions (running of secretions) of mucous membranes
Increasing nervous tissue integrity
Antiseptic and astringent
Previous uses: Root tea to increase appetite, soothing eyewash and soothing throats.

Myrrh gum, otherwise known as myrrha BP, myrrh Arabian, Somali myrrh, F. Myrrha, G. Myrrhe, and Sp. Mirra comes from the "commiphora species", and the Burseraceac family. Myrrh gum is from a hardy annual tree which thrives in Northeast Africa, Arabia, Abyssinia and Somaliland.

Myrrh

Myrrh is an aromatic, gummy substance with acid, bitter taste. The tree is 24″ high and likes moist rich soil and can be propagated. Herb dealers carry it in stocks. The myrrh tree composition is: 24-45% resin, 55-60% gum and 7-17% volatile oil. The gum is a natural plant hydrocolloid that is classified as a polysaccharide. It is a decomposition product of cellulose and associated with an oxydase. Myrrh gum composition is: ether soluble resins, ether insoluble resins, resenes and complex phenolic compounds. It is partly soluble in $H_2O$, alcohol and ether. Properties include: antiseptic, topical astringent, carminative, tonic and topical stimulant. Uses of myrrh gum have been in drugs, cosmetics, perfume, tooth powders, mouthwashes and by veterinarians to heal wounds of horses.

Lecithin

Lecithin is a phosphatide present in every living cell and contains glycerol, fatty acids, phosphoric acid and choline (see diagram). It is one of several waxy hydroscopic phosphatides that are widely distributed in plants and animals (as in nervous tissue). It swells up in $H_2O$ and NaCl, forming colloidal suspensions. Lecithin is an edible and digestible surfacant, anti-oxidant and emulsifier of natural origin. Fats are moved from the liver to cells with the aid of lecithin. Like cholesterol, lecithin is made in the body and because of its emulsifying properties has been widely used on the basis that its blood presence may dissolve cholesterol. In the body, lecithin phosphatides unite with iron, iodine and calcium to give power and vigor to the brain. It is found in the fatty protective covering of nervous tissue (myelin sheaths) and aids in a healthy nervous system. Lecithin has a high composition of inositol which occurs as a component of phospholipids and aids in the metabolism of fats. Cholone, one of the B vitamins is another basic constitute of lecithin and it functions with inositol to promote the health of the myelin sheaths of nerves and the transmission of nerve impulses.

Fatty substances such as soybeans, corn and egg yolk are very high in natural lecithin concentrations. Some uses of lecithin are in margerine, chocolate, pharmaceuticals, cosmetics and food additives.

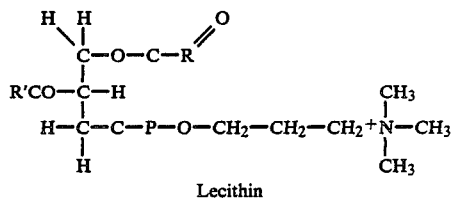
Lecithin

Lecithin granules such as "Leci-key" distributed by Carolson Division of J. R. Carlson Laboratories, Inc., Arlington Heights, Ill. are typical of the suitable lecithin materials for the packing material of this invention.

Any suitable goldenseal may be used, a typical suitable goldenseal composition useful in the formulation of this invention is hydrastis canadensis distributed by Natures Way Products, Inc., P.O. Box 2233, Provo, Utah.

Any suitable myrrh gum may be used in the packing formulation of this invention such as myrrh gum, balsamodendrom, distributed by Natures Way, Inc., P.O. Box 2233 Provo, Utah.

Any suitable wash solution may be used before applying the packing formulation of this invention. Some of the prior art washes that could be used are Uniwash, Hibiclens, a product of Stewart, Domeboros solution, a product of Miles, and Betadine, a product of Purdue Fredericks. It is highly preferred, however, that for best results the wash used in the present invention comprises hydrogen peroxide, normal saline solution, witch hazel and boric acid as described above. These materials are most effectively used when formulated in these proportions:

40% hydrogen peroxide
40% normal saline (sterile)
10% witch hazel
10% boric acid The following examples illustrate how the packing formulation of this invention can be used.

EXAMPLE I

The patient is positioned on his or her side for easy access to the decubitus ulcer. The ulcer is measured before treatment to be 4.5 cm×4.5 cm. The patient is irrigated first with a wash comprising 35 parts by weight $H_2O_2$, 35 parts normal saline solution, 15 parts witch hazel and 15 parts boric acid. After the ulcer is washed it is packed with a packing formulation which is a paste-like mixture comprising 35 parts by weight lecithin, 35 parts goldenseal and 30 parts myrrh gum. A sterile dressing is then applied over the packing formulation and left on for about four days. This same washing and packing treatment is repeated 3-4 times a week thereafter. About one month after the initial treatment the ulcer was reduced in size to 0.8 cm×0.8 cm×0.7 cm.

EXAMPLE II

The procedure of Example I is followed except the wash solution to be used will comprise 45 parts by weight $H_2O_2$, 45 parts normal saline, 5 parts witch hazel and 5 parts boric acid. The packing solution to be used contained 40 parts by weight lecithin, 40 parts goldenseal and 20 parts myrrh gum.

EXAMPLE III

The procedure of Example I is followed except the wash solution to be used contained 43 parts by weight $H_2O_2$, 43 parts normal saline, 7 parts witch hazel and 7 parts boric acid. The packing formulation comprises 35 parts lecithin, 35 parts myrrh gum and 30 parts goldenseal.

EXAMPLE IV

The procedure of Example I is followed except the wash to be used comprises 25 parts by weight $H_2O_2$, 25 parts normal saline, 10 parts witch hazel and 10 parts boric acid. The packing formulation comprises 50 parts lecithin, 50 parts goldenseal and 50 parts myrrh gum.

EXAMPLE V

A patient with a stage 3-4 decubitus ulcer has sinus areas reaching about 8 cm under the epidermis bilaterally. The exterior of this ulcer is 4.25 cm × 4.25 cm × 4.0 cm in size. The patient is allowed to turn on her side for free access to the ulcer. The ulcer is irrigated completely using a sterile syringe with a wash solution comprising 35 parts by weight $H_2O_2$, 35 parts normal saline, 15 parts witch hazel and 15 parts boric acid. The wash is repeated one time to ensure that the ulcer is properly cleansed. The ulcer is then packed with a packing formulation and covered with a sterile gauze dressing. The packing formulation comprises 33 parts by weight lecithin, 33 parts goldenseal and 33 parts myrrh gum.

This procedure is repeated three times a week for a one-month period. After one month from the original treatment the size of the ulcer is reduced to 0.8 cm × 0.8 cm × 0.7 cm with all sinus areas closed and healed. The average growth rate of tissue under this treatment is 1/16 inch per day.

EXAMPLE VI

The procedure of Example V is followed except the wash solution to be used will comprise 45 parts by weight $H_2O_2$, 45 parts normal saline, 5 parts witch hazel and 5 parts boric acid. The packing solution to be used contained 40 parts by weight lecithin, 40 parts goldenseal and 20 parts myrrh gum.

EXAMPLE VII

The procedure of Example V is followed except the wash solution to be used contained 43 parts by weight $H_2O_2$, 43 parts normal saline, 7 parts witch hazel and 7 parts boric acid. The packing formulation comprises 25 parts lecithin, 25 parts myrrh gum and 30 parts goldenseal.

EXAMPLE VIII

The procedure of Example V is followed except the wash to be used comprises 25 parts by weight $H_2O_2$, 25 parts normal saline, 10 parts witch hazel and 10 parts boric acid. The packing formulation comprises 50 parts lecithin, 50 parts goldenseal and 50 parts myrrh gum.

The preferred and optimumly preferred embodiment of the present invention has been described herein and shown to illustrate the underlying principles of the invention but it is to be understood that numerous modifications and ramifications may be made without departing from the spirit and scope of this invention.

What is claimed is:

1. A composition for treatment of decubitus ulcers comprising an admixture of from about 10 to about 50 parts lechithin, from about 10 to about 50 parts goldenseal root or rhizome, and from about 10 to about 50 parts myrrh gum.

2. The composition according to claim 1 wherein said admixture further comprises an effective amount of normal saline solution to form said goldenseal root or rhizome, myrrh gum and lecithin into a pastelike mixture.

3. The composition according to claim 1 wherein said admixture comprises from about 25 to about 40 parts lecithin, from about 25 to about 40 parts goldenseal root or rhizome and from about 25 to about 40 parts myrrh gum.

4. The composition according to claim 1 wherein said admixture comprises about one-third lecithin by weight, about one-third goldenseal root or rhizome by weight and about one-third myrrh gum by weight.

5. A method for treating a decubitus ulcer comprising the steps of:
   (a) contacting said decubitus ulcer with a washing solution; and
   (b) contacting said decubitus ulcer with an admixture comprising from about 10 to about 50 parts lecithin, from about 10 to about 50 parts goldenseal root or rhizome, and from about 10 to about 50 parts myrrh gum.

6. The method according to claim 5 wherein said washing solution comprises a solution of hydrogen peroxide, normal saline, witch hazel, and boric acid.

7. The method according to claim 5 wherein said washing solution comprises from about 10 to about 60 parts hydrogen peroxide, from about 10 to about 60 parts normal saline solution, from about 5 to about 15 parts witch hazel and from about 5 to about 15 parts boric acid.

8. The method according to claim 5 wherein said washing solution comprises about 40 parts hydrogen peroxide, about 40 parts normal saline, about 10 parts witch hazel and about 10 parts boric acid.

9. The method according to claim 5 wherein said admixture comprises 25 to 40 parts lecithin, 25 to 40 parts goldenseal root or rhizome, and 25 to 40 parts myrrh gum.

10. The method according to claim 5 wherein said admixture comprises about one-third lecithin by weight, about one-third goldenseal root or rhizome by weight and about one-third myrrh gum by weight.

* * * * *